US00PP15481P2

(12) United States Plant Patent
Robb

(10) Patent No.: US PP15,481 P2
(45) Date of Patent: Jan. 18, 2005

(54) LAVENDER PLANT NAMED 'BARCELONA ROSE'

(50) Latin Name: *Lavandula stoechas*
Varietal Denomination: Barcelona Rose

(75) Inventor: John B. Robb, Kariong (AU)

(73) Assignee: Paradise Seed Company, Kulnura (AU)

( * ) Notice: Subject to any disclaimer, the term of this patent is extended or adjusted under 35 U.S.C. 154(b) by 0 days.

(21) Appl. No.: 10/820,509

(22) Filed: Apr. 7, 2004

(51) Int. Cl.[7] ..... A01H 5/00
(52) U.S. Cl. ..... Plt./226

(58) Field of Search ..... Plt./226

(56) References Cited

U.S. PATENT DOCUMENTS

PP12,599 P2 * 4/2002 Cherry ..... Plt./226

* cited by examiner

*Primary Examiner*—Kent Bell
*Assistant Examiner*—W C Haas
(74) *Attorney, Agent, or Firm*—C. A. Whealy

(57) ABSTRACT

A new and distinct cultivar of Lavender plant named 'Barcelona Rose', characterized by its compact, upright and mounded plant habit; freely branching, dense and bushy plant form; and violet-colored flowers with showy light purple-colored terminal flower bracts.

1 Drawing Sheet

Botanical classification/cultivar designation: *Lavandula stoechas* cultivar Barcelona Rose.

BACKGROUND OF THE INVENTION

The present Invention relates to a new and distinct cultivar of Lavender plant, botanically known as *Lavandula stoechas,* and hereinafter referred to by the name 'Barcelona Rose'.

The new Lavender is a product of a planned breeding program conducted by the Inventor in Kulnura, New South Wales, Australia. The objective of the breeding program was to create new compact and freely branching Lavender cultivars with large and attractive flowers and good garden performance.

The new Lavender originated from a cross-pollination made by the Inventor in August, 1999, of the *Lavandula stoechas* cultivar Madrid Pink, not patented, as the female, or seed, parent with an unknown selection of *Lavandula stoechas,* not patented, as the male, or pollen, parent. The new Lavender was discovered and selected by the Inventor as a single flowering plant within the progeny of the stated cross-pollination grown in a controlled environment in Kulnura, New South Wales, Australia in 1999.

Asexual reproduction of the new cultivar by terminal cuttings taken at Kulnura, New South Wales, Australia, since October, 2000, has shown that the unique features of this new *Lavender* are stable and reproduced true to type in successive generations.

SUMMARY OF THE INVENTION

Plants of the cultivar Barcelona Rose have not been observed under all possible environmental conditions. The phenotype may vary somewhat with variations in environment such as temperature and light intensity without, however, any variance in genotype.

The following traits have been repeatedly observed and are determined to be the unique characteristics of 'Barcelona Rose'. These characteristics in combination distinguish 'Barcelona Rose' as a new and distinct cultivar:

1. Compact, upright and mounded plant habit.
2. Freely branching, dense and bushy plant form.
3. Violet-colored flowers with showy light purple-colored terminal flower bracts.

Plants of the new Lavender differ from plants of the female parent, the cultivar Madrid Pink, in the following characteristics:

1. Plants of the new Lavender are more dense than plants of the cultivar Madrid Pink.
2. Plants of the new Lavender have shorter peduncles than plants of the cultivar Madrid Pink.
3. Plants of the new Lavender flower later than plants of the cultivar Madrid Pink.

Plants of the new Lavender can be compared to plants of the cultivar Kew Red, not patented. In side-by-side comparisons conducted by the Inventor in Kulnura, New South Wales, Australia, plants of the new Lavender differed from plants of the cultivar Kew Red in the following characteristics:

1. Plants of the new Lavender were denser and bushier than plants of the cultivar Kew Red.
2. Plants of the new Lavender had longer terminal flower bracts than plants of the cultivar Kew Red.
3. Plants of the new Lavender flowered later than plants of the cultivar Kew Red.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Lavender.

The photograph at the bottom of the sheet comprises a side perspective view of a typical flowering plant of 'Barcelona Rose' grown in a one-gallon container.

The photograph at the top of the sheet comprises a close-up view of typical leaves and inflorescences of 'Barcelona Rose'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown under conditions which closely approximate commercial production conditions during the winter in a polycarbonate-covered greenhouse in Lompoc, Calif. for about 37 weeks in 1-gallon containers. During the production of the plants, day temperatures ranged from 18 to 24° C., night temperatures ranged from 16 to 18° C., and light levels ranged from 4,000 to 8,000 foot-candles.

Botanical classification: *Lavandula stoechas* cultivar Barcelona Rose.

Parentage:

*Female parent.*—*Lavandula stoechas* cultivar Madrid Pink, not patented.

*Male parent.*—Unknown selection of *Lavandula stoechas,* not patented.

Propagation:

*Type cutting.*—Terminal vegetative cuttings.

*Time to initiate roots.*—Summer: About one week at 25° C. Winter: About two weeks at 20° C.

*Time to produce a rooted young plant.*—Summer: About six weeks at 25° C. Winter: About seven weeks at 20° C.

*Root description.*—Fine, fibrous, and freely branching.

Plant description:

*Form.*—Perennial. Compact, upright and mounded plant form. Freely branching, about eight main stems each with about six lateral branches; dense and bushy plant habit; vigorous growth habit. Flowers in verticillasters on crowded spikes with showy terminal flower bracts.

*Plant height.*—About 20 cm.

*Plant width.*—About 36 cm.

*Lateral branch description.*—Length: About 22 cm. Diameter: About 6 mm. Internode length: About 1.3 cm. Strength: Strong. Aspect: Mostly upright to somewhat outwardly spreading. Texture: Fine pubescence. Color: Developing stems: 193A. Older woody stems: 200D.

*Foliage description.*—Arrangement: Opposite, simple; sessile. Length: About 3.9 cm. Width: About 4 mm. Shape: Linear. Apex: Broadly acute. Base: Attenuate, clasping. Margin: Entire. Texture, upper and lower surfaces: Pubescence. Fragrance: Very aromatic, pungent. Venation pattern: Pinnate. Color: Developing and fully expanded foliage, upper surface: 189A. Developing and fully expanded foliage, lower surface: 191A. Venation, upper and lower surfaces: 194A.

Flower description:

*Flower arrangement and shape.*—Small single flowers in compact verticillasters on crowded spikes. Freely flowering, about 84 flowers per spike; flowers tubular with five lobes; inflorescences with showy terminal bracts.

*Natural flowering season.*—Continuous throughout the Spring. Flower longevity on the plant: Individual inflorescences last about two weeks on the plant and individual flowers last about three to four days on the plant. Flowers not persistent, terminal flower bracts persistent.

*Flower buds.*—Length: About 6 mm. Diameter: About 2.5 mm. Shape: Oblong. Color: 79A.

*Inflorescence size.*—Length: About 4 cm. Diameter: About 1.7 cm.

*Flowers.*—Diameter: About 5 mm. Depth (height): About 1.2 cm.

*Petals.*—Arrangement: Five, fused into a tube. Length, lobes: About 2 mm. Width, lobes: About 2 mm. Shape: Roughly spatulate. Apex: Rounded. Margin: Entire. Texture, upper and lower surfaces: Smooth, velvety. Color: When opening, upper surface: 79A. When opening, lower surface: 79C. Fully opened, upper surface: 83A. Fully opened, lower surface: 83B.

*Terminal flower bracts.*—Arrangement: About six in a single whorl at inflorescence apex. Length: About 1.8 cm. Width: About 8 mm. Shape: Obovate. Apex: Acute. Base: Attenuate. Margin: Entire. Texture, upper and lower surfaces: Smooth. Color, immature, upper and lower surfaces: 75B. Color, mature, upper and lower surfaces: 75A to 75B.

*Flower bracts.*—Arrangement: Each whorl of flowers subtended by a flower bract. Length: About 5 mm. Width: About 5 mm. Shape: Tri-lobed. Apex: Rounded. Base: Truncate. Margin: Entire. Texture, upper and lower surfaces: Smooth. Color, upper and lower surfaces: 191B; venation, 189A.

*Calyx.*—Arrangement: Five sepals fused into a tube. Length: About 5 mm. Width: About 2 mm. Sepal apex: Acute. Color, upper and lower surfaces: 194A.

*Peduncle.*—Strength: Strong. Length: About 3.3 cm. Diameter: About 2 mm. Aspect: Mostly upright. Color: 194A.

*Reproductive organs.*—Stamens: Quantity per flower: Four. Anther shape: Oval. Anther length: Less than 1 mm. Anther color: 17A. Pollen amount: Scarce. Pollen color: 17A. Pistils: Quantity per flower: One. Pistil length: About 6 mm. Stigma shape: Rounded. Stigma color: 79A. Style length: About 3 mm. Style color: 155A. Ovary color: 194A.

*Seed/fruit.*—Seed and fruit production has not been observed.

Disease/pest resistance: Plants of the new Lavender have not been noted to be resistant to pathogens and pests common to Lavender.

Weather tolerance: Plants of the new Lavender have exhibited good tolerance to rain and wind and have been observed to tolerate temperatures from −2 to 40° C.

It is claimed:

1. A new and distinct cultivar of Lavender plant named 'Barcelona Rose', as illustrated and described.

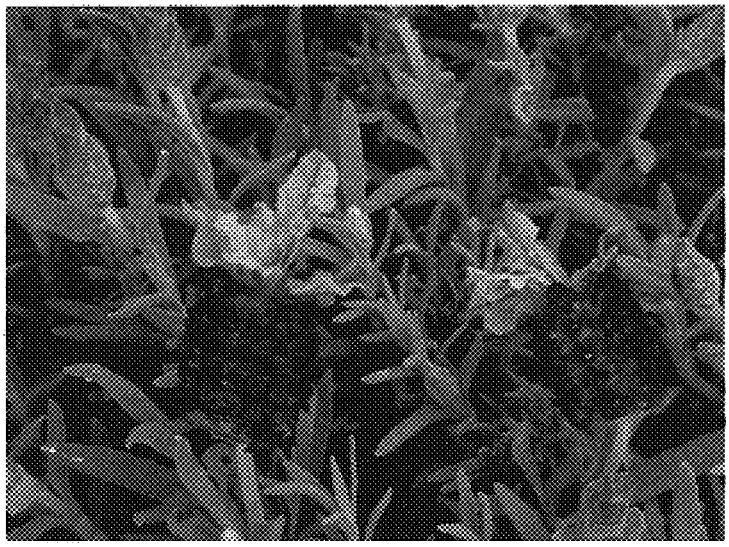
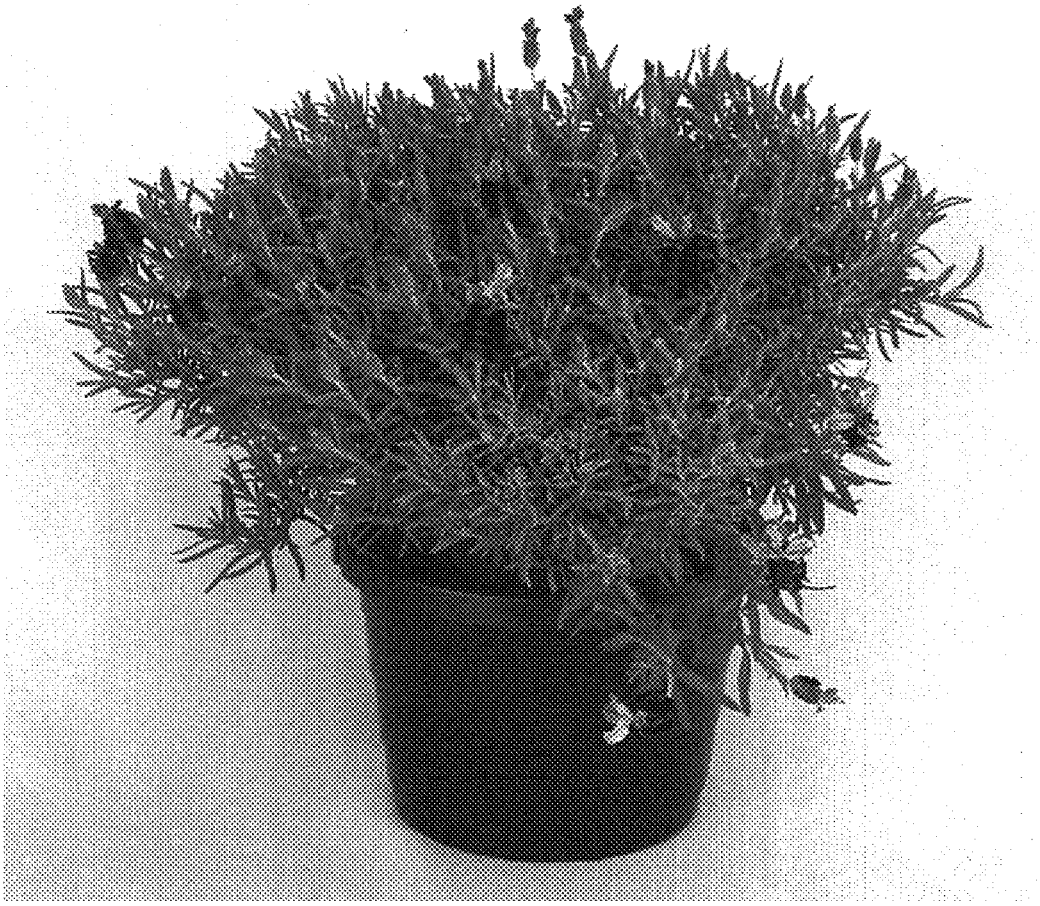

* * * * *